United States Patent
Dahms

(10) Patent No.: US 10,226,416 B2
(45) Date of Patent: Mar. 12, 2019

(54) HAIR CONDITIONING COMPOSITION FOR PERMANENT AND SEMI-PERMANENT HAIR COLORATION APPLICATIONS

(71) Applicant: CLARIANT INTERNATIONAL LTD., Muttenz (DE)

(72) Inventor: Gerd Herbert Dahms, Duisburg (DE)

(73) Assignee: Clariant International Ltd., Muttenz (CH)

( * ) Notice: Subject to any disclaimer, the term of this patent is extended or adjusted under 35 U.S.C. 154(b) by 0 days.

(21) Appl. No.: 14/387,891

(22) PCT Filed: Mar. 22, 2013

(86) PCT No.: PCT/EP2013/056021
§ 371 (c)(1),
(2) Date: Sep. 25, 2014

(87) PCT Pub. No.: WO2013/143989
PCT Pub. Date: Oct. 3, 2013

(65) Prior Publication Data
US 2015/0056154 A1 Feb. 26, 2015

(30) Foreign Application Priority Data
Mar. 26, 2012 (EP) .................... 12161349

(51) Int. Cl.
| | | |
|---|---|---|
| A61K 8/64 | (2006.01) | |
| A61Q 5/12 | (2006.01) | |
| A61K 8/97 | (2017.01) | |
| A61Q 5/10 | (2006.01) | |
| A61K 8/65 | (2006.01) | |
| A61K 8/34 | (2006.01) | |
| A61K 8/86 | (2006.01) | |
| A61Q 5/06 | (2006.01) | |

(52) U.S. Cl.
CPC ............ *A61K 8/97* (2013.01); *A61K 8/34* (2013.01); *A61K 8/345* (2013.01); *A61K 8/64* (2013.01); *A61K 8/645* (2013.01); *A61K 8/65* (2013.01); *A61K 8/86* (2013.01); *A61Q 5/10* (2013.01); *A61Q 5/12* (2013.01); A61Q 5/065 (2013.01)

(58) Field of Classification Search
None
See application file for complete search history.

(56) References Cited

U.S. PATENT DOCUMENTS

| | | | |
|---|---|---|---|
| 4,080,310 A | 3/1978 | Ng et al. | |
| 4,141,888 A | 2/1979 | Matsuda | |
| 4,186,188 A | 1/1980 | Gumprecht | |
| 4,190,064 A | 2/1980 | Gordon et al. | |
| 4,279,996 A | 7/1981 | Holtzapple | |
| 4,423,032 A | 12/1983 | Abe et al. | |
| 4,436,722 A | 3/1984 | Matsunaga et al. | |
| 4,495,173 A | 1/1985 | Matsunaga et al. | |
| 4,530,829 A * | 7/1985 | Abe .................. | A61K 8/65 424/70.14 |
| 4,591,497 A | 5/1986 | Naito et al. | |
| 5,538,720 A | 7/1996 | Jendryssek-Pfaff et al. | |
| 5,738,879 A * | 4/1998 | Rine .................. | A61K 8/19 424/401 |
| 5,972,177 A | 10/1999 | Brehm et al. | |
| 5,981,450 A | 11/1999 | Fabry et al. | |
| 6,013,250 A | 1/2000 | Cannell | |
| 6,106,815 A | 8/2000 | Kang | |
| 6,218,459 B1 | 4/2001 | Gruning et al. | |
| 7,829,514 B2 | 11/2010 | Paul et al. | |
| 2004/0210039 A1 | 10/2004 | Schrooyen et al. | |
| 2010/0202936 A1 | 8/2010 | Yoshioka | |
| 2014/0225021 A1 | 8/2014 | Dahms et al. | |
| 2014/0323702 A1 | 10/2014 | Dahms et al. | |
| 2015/0306016 A1 | 10/2015 | Dahms | |

FOREIGN PATENT DOCUMENTS

| | | |
|---|---|---|
| CN | 101411676 | 4/2009 |
| DE | 695940 C | 9/1940 |
| DE | 9211006 U1 | 12/1993 |
| DE | 4433071 C1 | 12/1995 |
| DE | 19619661 A1 | 11/1997 |
| DE | 102005031467 A1 | 1/2007 |
| DE | 102010001193 A1 | 7/2011 |
| DE | 102011055889 A1 | 6/2013 |
| EP | 0057837 A2 | 8/1982 |
| EP | 0499261 A1 | 8/1992 |

(Continued)

OTHER PUBLICATIONS

MakingCosmetics ("How to Make Hair Conditioners," MakingCosmetics Inc., one page, (May 2, 2006)) accessed Oct. 5, 2015 at URL makingcosmetics.com/articles/23-how-to-make-hair-conditioners.pdf).*

Annette F. Dexter et al: "Peptides As Functional Surfactants", Industrial & Engineering Chemistry Research, vol. 47, No. 17, Sep. 3, 2008 (Sep. 3, 2008), pp. 6391-6398.

Cardamone et al: "Investigating the microstructure of keratin extracted from wool: Peptide sequence (MALDI-TOF/TOR) and protein conformation (FTIR)", Journal of Molecular Structure, Elsevier, Amsterdam, NL,vol. 969, No. 1-3, Apr. 22, 2010 (Apr. 22, 2010), pp. 97-105.

Mokrejs, Pavel et al: Producing Keratin Hydrolysates from Sheep Wool, Oriental Journal of Chemistry, Oct. 2011 (Oct. 2011), pp. 1303-1309.

(Continued)

*Primary Examiner* — Julie Ha
*Assistant Examiner* — Kristina M Hellman
(74) *Attorney, Agent, or Firm* — Tod A. Waldrop

(57) ABSTRACT

The disclosure concerns a hair conditioning composition for permanent and semi-permanent hair color applications wherein the hair conditioning composition comprises a solvent; a water-soluble, oligo-peptide from a natural proteinous raw-material source containing Sulfur; alkaline or alkaline earth metal ions; a multidentate ligand or chelating agent and optionally a redox-active inorganic or organic component.

18 Claims, 2 Drawing Sheets

(56) References Cited

FOREIGN PATENT DOCUMENTS

| | | |
|---|---|---|
| EP | 0959093 A1 | 11/1999 |
| GB | 2061956 | 5/1981 |
| GB | 2061956 A | 5/1981 |
| JP | S56-073095 | 6/1981 |
| JP | S57-130910 | 8/1982 |
| JP | S62-053909 | 3/1987 |
| JP | S64-019013 | 1/1989 |
| JP | H0515761 A | 1/1993 |
| JP | H06107997 A | 4/1994 |
| JP | H07-069835 | 3/1995 |
| JP | H11-269045 | 10/1998 |
| JP | 2000-502677 | 7/2000 |
| JP | 2001-031697 | 2/2001 |
| JP | 2001-525822 | 12/2001 |
| JP | 2002-114643 | 4/2002 |
| JP | 2002235095 A | 8/2002 |
| JP | 2002-322035 | 11/2002 |
| JP | 2003-040745 | 2/2003 |
| JP | 2004113976 A | 4/2004 |
| JP | 2004-323423 | 11/2004 |
| JP | 2005-120286 | 5/2005 |
| JP | 2006-273782 | 10/2006 |
| JP | 2008050279 A | 3/2008 |
| JP | 2008-074727 | 4/2008 |
| JP | 2009534392 A | 9/2009 |
| JP | 2010-037283 | 2/2010 |
| JP | 2010-105926 | 5/2010 |
| JP | 2010-235572 | 10/2010 |
| RO | 101787 A2 | 12/1991 |
| SU | 535339 | 11/1976 |
| WO | WO-97-023194 A1 | 7/1997 |
| WO | WO-97/36500 A1 | 10/1997 |
| WO | WO-02/36801 A2 | 5/2002 |
| WO | WO-03/006531 A1 | 1/2003 |
| WO | WO-2009-000057 A2 | 12/2008 |

OTHER PUBLICATIONS

Eremeev, N. L. et al: "Enzymatic hydrolysis of keratin-containing stock for obtaining protein hydrolysates", Applied Biochemistry and Microbiology, vol. 45, No. 6, Nov. 1, 2009 (Nov. 1, 2009), pp. 648-655.
Rouse, Jillian G. et al: "A Review of Keratin-Based Biomaterials for Biomedical Applications", Materials, vol. 3, No. 2, Feb. 3, 2010 (Feb. 3, 2010), pp. 999-1014.
Database GNPD [Online] Mintel; Feb. 2009 (Feb. 2009), "Permanent Hair Colourant", XP002685950, retrieved from http://www.gnpd.com Database accession No. 1047995, the whole document.
Database GNPD [Online] Mintel; Jun. 2011 (Jun. 2011, "Abundant Volume Shampoo", XP002685951, retrieved from http://www.gnpd.com Database accession No. 1553940 the whole document.
Database GNPD [Online] Mintel; Mar. 2007 (Mar. 2007), "PM Repair Strenghtener", XP002685952, retrieved from http://www.gnpd.com Database accession No. 677492 the whole document.
Database GNPD [Online] Mintel; 2009 (Sep. 2009), "Shampoo", XP002685953, retrieved from http://www.gnpd.com Database accession No. 1172585 the whole document.
Database GNPD [Online] Mintel; Oct. 2011 (Oct. 2011), "Conditioner", XP002685954, retrieved from http://www.gnpd.com Database accession No. 1655880 the whole document.
Machine language translation of DE 10000388, Jan. 1957.
Machine language translation of JPS5551095, Apr. 1980.
Manzur, A; Spelzini, D; Farruggia, B; Romanini, D; Pico, G "Polyethyleneimine phosphate and citrate systems act like pseudo polyampholytes as a starting method to isolate pepsin" J. Chrom. B, 2007 (pub online Oct. 22, 2007) 860(1), p. 63-68, doi:10.1016/j.jchromb.2007.10.013.
Sulpizio, Thomas E, "Advances in Fiter Aid Precoat Filtration Technology" Conference of the American Filtration and Separation Society, Apr. 6-9, 1999. 16 pages.
English Abstract for SU535399, Nov. 15, 1976.
International Search Report for PCT/EP2012/004940, dated Mar. 20, 2013.
International Preliminary Report on Patentability for PCT/EP2012/004940, dated Jun. 3, 2014.
Non-Final Rejection for U.S. Appl. No. 14/355,453, dated Jan. 4, 2016.
Final Rejection for U.S. Appl. No. 14/355,453, dated Sep. 22, 2016.
Non-Final Rejection for U.S. Appl. No. 14/355,453, dated Sep. 8, 2017.
English Abstract for JP 2001-031697, Feb. 6, 2001.
English Abstract for JP 2002-114643, Apr. 6, 2002.
English Abstract for JP 2002-322035, Nov. 11, 2002.
English Abstract for JP 2003-040745, Feb. 13, 2003.
English Abstract for JP 2004-323423, Nov. 18, 2004.
English Abstract for JP 2005-120286, May 12, 2005.
English Abstract for JP 2006-273782, Oct. 12, 2006.
English Abstract for JP 2008-074727, Apr. 3, 2008.
English Abstract for JP 2010-037283, Feb. 18, 2010.
English Abstract for JP 2010-105926, May 13, 2010.
English Abstract for JP 2010-235572, Oct. 21, 2010.
English Abstract for JP H11-269045, Oct. 5, 1998.
English Abstract for JP S62-053909, Mar. 9, 1987.
English Abstract for JP S64-019013, Jan. 23, 1989.
Introduction of New Raw Material Wool-Derived Keratin with Excellent Conditioning Function, Fragrance Journal, published on Apr. 15, 2005 (H17), Apr. 2005 issue (vol. 33, No. 4), 295th issue.
English Translation of "Introduction of New Raw Material Wool-Derived Keratin with Excellent Conditioning Function", Fragrance Journal, published on Apr. 15, 2005 (H17), Apr. 2005 issue (vol. 33, No. 4), 295th issue.

* cited by examiner

HAIR CONDITIONING COMPOSITION FOR PERMANENT AND SEMI-PERMANENT HAIR COLORATION APPLICATIONS

CROSS-REFERENCE TO RELATED APPLICATIONS

This application is a National Stage of International Application No. PCT/EP2013/056021, filed on Mar. 22, 2013, and published in English as WO 2013/143989 A1 on Oct. 3, 2013. This application claims the benefit and priority of European Application No. 12161349.1, filed on Mar. 26, 2012. The entire disclosures of the above applications are incorporated herein by reference.

BACKGROUND

This section provides background information related to the present disclosure which is not necessarily prior art.

FIELD OF THE INVENTION

The present invention relates to a hair conditioning composition for permanent and semi-permanent hair coloration application and the use of such hair conditioning composition and a kit of parts containing said composition.

BACKGROUND OF THE INVENTION

It is known from real life and a large number of publications and patents that various treatments targeting the hair in a beauty care will cause the hair to be damaged. Among those hair care treatments often blow-drying, semi-permanent or permanent hair dying or bleaching and perm is found. Those kinds of treatments do chemically and physically alter the hair structure, which might be followed by reduced hair flexibility, causing split ends or broken hair. In addition some of the mentioned hair treatments do only change the hair condition for a limited period of time. Although it is obvious that the hair growth itself might limit the duration of the effect of the hair treatment, in certain cases pre- in between- or post-hair care treatment can be provided, leading to a better and/or longer lasting result.

One possible solution to overcome or reduce the hair damage caused by the treatment and to extend the intended beauty effects is the use of proteinous substances in the treatment, which do interact with the hair keratin, resulting in a kind or protection or repair process.

For instance one solution is given by the U.S. Pat. No. 4,436,722, disclosing a hair rinse composition which comprises at least one cationic surface active agent and a decomposition derivative of a keratin material which have been dissolved or dispersed in a suitable solvent. The decomposition derivative is a member selected from hydrolysates of keratin material, alkali salts of decomposition products obtained by oxidation of keratin material, alkali salts of derivatives at a thiol group of decomposition products obtained by reduction of keratin material and a mixture thereof.

Another approach is illustrated by the U.S. Pat. No. 4,186,188, using polypeptides with sterically unhindered positive charges, which can be incorporated into a cosmetic formulation for human hair, skin and nails. The polypeptides, which can be prepared by trypsin catalyzed hydrolysis of protein provide a molecular weight of the polypeptide of from about 200 to about 2,000 Da.

Further on, U.S. Pat. No. 4,279,996 describes a water-soluble keratin hydrolyzate having at least two mercapto-groups in one molecule and having an average molecular weight of 2 000 to 20 000 Da, which shall be suitable for cosmetic application to the hair particularly as hair fixatives. The hydrolyzate is prepared by reducing keratin in an aqueous solution of a reducing agent under alkaline conditions and subjecting the resulting reduction product to enzymatic hydrolysis.

In addition U.S. Pat. No. 4,423,032 is using hair treatments comprising defined amounts of two ingredients, one of which being at least one decomposition derivative of keratin material such as hydrolysates of keratin material, alkali salts of decomposition products obtained by oxidation of keratin material and alkali salts of derivatives at the thiol group of decomposition products obtained by reduction of keratin material. The other is at least one silicone derivative of a specific type.

A pre-shampoo type hair treatment is disclosed by U.S. Pat. No. 4,495,173, which comprises at least one decomposition derivative of keratin material selected from hydrolysates of keratin material, alkali salts of decomposition products obtained by oxidation of keratin material and alkali salts of derivatives at the thiol-group of decomposition products obtained by reduction of keratin material, the at least one decomposition derivative having been dissolved or dispersed in suitable solvent.

Nevertheless, none of the above mentioned patent documents is able to disclose a hair care composition, adding a number of special benefits to a permanent and/or semi-permanent hair coloration application, i.e. shortening of the overall treatment time, more even color distribution, increased hair protection, better hair shine, gloss, brilliance and hair coloration durability.

SUMMARY OF THE INVENTION

In order to overcome the shortcomings of the state of the art and to combine hair protection and increase the evenness, efficiency and durability of permanent and semi-permanent hair color applications the present invention discloses a hair conditioning composition characterized in that the composition comprises a solvent; a water-soluble, oligo-peptide from a natural proteinous raw-material source containing Sulfur; alkaline or alkaline earth metal ions; a multidentate ligand or chelating agent and optionally a redox-active inorganic or organic component.

DETAILED DESCRIPTION OF THE PREFERRED EMBODIMENTS

Surprisingly it has been found, that the application of a combination of several active principles in an aqueous environment to the hair is able to result in effective hair protection and better and longer lasting hair coloration. This result is achieved by using a hair conditioning composition for permanent and semi-permanent hair color applications characterized in that the hair conditioning composition comprises a solvent; a water-soluble, oligo-peptide from a natural proteinous raw-material source containing Sulfur, alkaline or alkaline earth metal ions, a multidentate ligand or chelating agent and optionally a redox-active inorganic or organic component.

The hair conditioning composition in the sense of the invention is any cosmetic or pharmaceutical composition; either in liquid or dry (powder) form, which can be used in a hair treatment in any known form including pre-shampoo;

shampoo, hair rinse, mousse, hair setting lotion, hair liquid, hair tonic, air brushing lotion; hair spray and the like.

The composition can preferably be used in permanent or semi-permanent hair coloration application. Semi-permanent and permanent hair coloration processes do differ from temporary hair coloration by the use of special dyes, which can be chemically fixed to the hair structure. This in contrast to temporary hair dyes, which are only physically bound to the hair structure and can be easily removed during hair washing. Usually semi-permanent hair dyes may survive two-ten hair shampooing/washing procedures and permanent hair days will stay for longer than approximately 10 washings.

Several different permanent hair dyes can be found on the market which may be used in combination of the inventive hair conditioning composition. Among the dyes may be, without being limited to this special kind of dyes, for instance direct hair dyes, either as cationic, anionic or neutral dyes.

Suitable non-limiting examples for anionic hair dyes are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Non-limiting examples to cationic dyes are Basic Blue 6, Basic Blue 7, Basic Blue 9, Basic Blue 26, Basic Blue 41, Basic Blue 99, Basic Brown 4, Basic Brown 16, Basic Brown 17, Basic Orange 31, Natural Brown 7, Basic Green 1, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 57 and Basic Yellow 87.

Further suitable dyes for colouring hair within the meaning of the present invention are those of neutral nitro dyes. Suitable non-limiting examples are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Plant dyestuffs may also be used as hair colorant within the meaning of the present invention for example henna (red or black), alkanna root, laccaic acid, indigo, logwood powder, madder root and rhubarb powder, etc.

The solvent in the sense of the invention can be either water, an organic solvent, a synthetic oil component, a volatile/non volatile silicon-component or any mixture thereof.

Water used in the present invention is not limited in particular and the specific examples include mineral water, spring water, tap water, deionized water, distilled water, water for injection (WFI) or a combination thereof.

The compositions of the present invention can contain one or more organic solvents, suitable ones are ethanol, propanol, isopropanol, isopentane, n-pentane, n.hexane, dimethoxymethane, benzyl alcohol, benzyloxyethanol, alkylene carbonates such as ethylene carbonate and propylene carbonate, phenoxyethanol, butanol, isobutanol, cyclohexane, cyclohexanol, ethylenecarbonate, ethyleneglycol monoethylether, ethylene glycol monobutyl ether, ethylene glycol monophenyl ether, 1-phenylethylalcohol, 2-phenylethylalcohol, o-methoxyphenol.

The most preferred organic solvents are ethanol, isopropanol and propanol.

Further, suitable synthetic oil components are in particular fatty alcohol fatty acid esters such as isopropyl myristate, palmitate, stearate and isostearate, oleyl oleate, isocetyl stearate, hexyl laurate, dibutyl adipate, dioctyl adipate, myristyl myristate, oleyl erucate, polyethylene glycol and polyglyceryl fatty acid esters, cetyl palmitate, etc.

Here again any silicone oil, either volatile and/or non-volatile, is suitable for the compositions of the present invention. Preferred silicone oils are non-volatile silicone oils known with their INCI name as dimethicone and dimethiconol. Volatile silicone oils such as cyclomethicones may be used in combination with non-volatile silicones and/or other wax and/or oils mentioned above. Commercially, they are available from various companies for example Dow Corning with the known DC series, Wacker Chemie and Toray silicones. All commercially available non volatile silicones are suitable in the compositions of the present invention. Furthermore, aminated silicones such as amodimethicone and arylated silicones comprising at least one aryl group in its molecule such as phenyl methicone, phenyl trimethicone, diphenyl dimethicone, diphenylsiloxy phenyl trimethicone, tetramethyl tetraphenyl trisiloxane, triphenyl trimethicone, tetramethyl tetraphenyl trisiloxane and trimethyl pentaphenyl trisiloxane can be advantageously comprised in the compositions of the present invention.

The water-soluble, oligo-peptide from a natural proteinous raw-material source containing Sulfur may be derived from any natural raw material source, either plant based or animal based. Preferably the raw material source is re-newable, i.e. ecologically friendly, and the oligo-peptide can be derived from the natural raw material by an extraction and degradation process as described in DE 10 2011 055 889. The oligo-peptide in the meaning of this invention is an organic molecule containing from 2 to about 100 amino acid subunits.

As used herein, the term "amino acid" is intended to include not only the L-, D- and nonchiral forms of naturally occurring amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine), but also modified amino acids, amino acid analogs, and other chemical compounds which can be incorporated in conventional oligopeptide synthesis, e.g., 4-nitrophenylalanine, isoglutamic acid, isoglutamine, epsilon-nicotinoyl-lysine, isonipecotic acid, tetrahydroisoquinoleic acid, alpha-aminoisobutyric acid, sarcosine, citrulline, cysteic acid, t-butylglycine, t-butylalanine, phenylglycine, cyclohexylalanine, beta-alanine, 4-aminobutyric acid, and the like. It is especially preferred, that the oligo-petide comprises amino-acids containing sulfur in the amino-acid side chain.

One preferred animal derived starting material is keratin. The keratin starting materials may be derived for example from animal hairs, human hair, feathers, hooves, claws, horns, scales and the like. Of these, wool, human hair and feathers are preferably used. These keratin materials may be subjected to the oxidation or reduction reaction as they are but if necessary, they may be cut or reduced into pieces having a suitable size or subjected to pre-treatments such as washing and defatting.

Other plant derived starting material may be Garbanzo beans, kidney beans, lentils, lima beans, navy beans, soybeans, Barley, brown rice, buckwheat, millet, oatmeal, quinoa, rye, wheat germ, wheat or wild rice.

In the hair care composition also alkaline or alkaline earth metal ions are present in a solvated "free" or ionically attached form. As alkali or alkaline earth metal ions for example sodium, potassium, rubidium, cesium, magnesium, calcium, lithium or barium can be used.

Optionally, the alkali or alkaline earth metal ions can be introduced into the inventive composition in the form of a salt of α-hydroxy acids, like e.g. lactic acid.

One further component in the hair care composition is a multidentate ligand or chelating agent. Among the chelating agents that can be used in the composition of the disclosure, exemplary mention may be made of: tricarboxylic or tetracarboxylic acids or salts thereof for example, methyl glycine diacetic acid, N-lauroyl ethylenediamine-N,N',N'-triacetic acid, iminodisuccinic acid, N,N-dicarboxymethyl-L-glutamic acid, ethylenediamine-N,N'-dissucinic acid, ethylenediaminetetraacetic acid (EDTA), citric acid; phosphonic derivatives such as hexamethylenediaminetetra(methylenephosphonic) acid, ethylenediaminetetra(methylenephosphonic) acid, 1-hydroxyethylidene-1,1-diphosphonic acid, aminotri(methylenephosphonic) acid, diethylenetriaminepenta (methylenephosphonic) acid, and salts thereof and for example, the sodium salts thereof such as the pentasodium salt of ethylenediaminetetra(methylenephosphonic) acid; dendrimers having a chelating activity; proteins such as spermine, spermidine, transferrin, ferritin; monocarboxylic or dicarboxylic acids or salts thereof such as phytic acid, malic acid, nitriloacetic acid, fumaric acid, tartaric acid, succinic acid, oxalic acid, mucic acid; desferrioxamine mesylate; and mixtures of these multidentate ligands or chelating agents.

In addition the hair conditioning composition comprises optionally a redox-active inorganic or organic component. The redox-active inorganic or organic component may either provide oxidizing or reducing properties in aqueous solution, i.e. may either be capable of reducing another substance or may be capable of oxidizing that other substance. The reduction of that other substance may be caused by donating an electron to that other substance and the oxidation of that other substance may be caused by accepting an electron from the other substance. As a result of the oxidation/reduction reaction the redox-active inorganic or organic component also changes its oxidation state respectively. Without being bound by the theory the redox-potential of the hair conditioning composition might help to effectively attach the dye substances to the hair or might help trapping the dye molecules physically in the hair structure.

In a preferred embodiment of the invention the hair conditioning composition exhibits a redox-potential E in the range of $E \leq +500$ mV and $E \geq -1000$ mV. More preferably, the hair conditioning composition exhibits a redox-potential $E \leq 0$ mV and $E \geq -1000$ mV and most preferably the hair conditioning composition exhibits a redox-potential $E \leq -10$ mV and $E \geq -750$ mV. The redox-potential is given in Volts or milli-Volts and measured against the standard hydrogen electrode at a temperature of 298.15 K (25° C.).

In another preferred embodiment of the invention the hair conditioning composition further comprises a cationic quaternary surface active agent. A quaternary surface active agent is defined as being a polyatomic cationic ion of the general structure $NR_4^+$, whereas R being either a hydrogen or an aliphatic or aromatic side chain. The aliphatic or aromatic side chain may in addition be substituted or may contain unsaturated double or triple bonds. Preferable examples of the quaternary ammonium salts include distearyldimethylammonium chloride, stearyltrimethylammonium methosulfate, stearyltrimethylammonium chloride, stearyldimethylbenzylammonium chloride, lauryldiethylbenzylammonium chloride, lauryltrimethylammonium bromide, distearylmethylhydroxymethylammonium chloride, cetyltrimethylammonium chloride and the like. Furthermore, the hair conditioning composition may comprise a silicon quaternary compound, like Quaternium 80, commercially available by Evonik Industries.

In addition the hair conditioning composition may contain further organic molecules, which may provide additional cosmetics benefits or may alter the interaction of the hair care dyes. Especially preferred are in general alcohols having 1-5 carbon atoms, propylene glycol and glycerine or any mixture thereof. Of course it is obvious that also solutions of water containing such kinds of alcohols can be included.

Another preferred embodiments of the invention may be found in a hair conditioning composition according characterized in that the hair conditioning composition contains from $\geq 1\%$ (w/w) to $\leq 10\%$ (w/w) of water-soluble oligo-peptides. The total content of the water soluble oligo-peptide may be determined using any kind of method suitable for protein determination. The determination can be carried out either in the solution or after an organic washing and precipitation step. Suitable methods may include Bradford-, Lowry-, Biuret- or simple UV-techniques. The overall oligo-peptide content is chosen with respect to efficacy, targeted effect in the hair care application and overall viscosity requirements.

In another aspect of the invention the molecular weight of the oligo-peptides is preferably in the range of $1000\ Da \leq MW \leq 10\ 000$ Da, more preferably in the range of $2000\ Da \leq MW \leq 8000$ Da and most preferably in the range of $3000\ Da \leq MW \leq 7000$ Da. Without being bound to the theory the molecular weight is one parameter which determines the ability of the oligo-peptide to interact with the hair. Higher molecular weight indicates larger molecules, which in turn are less likely to diffuse into the hair-structures. Large peptides will stay on the hair and form a film. Surprisingly it has been found, that the chosen molecular weight range is suitable to provide both features. The oligo-peptide is able to penetrate into the hair structure and fill up voids and, in addition, the peptides are able to interact on the top of the hair structure and form a film. Further on, the oligo-peptide is able to interact with organic or inorganic dyes in the manner of a co-acervate, resulting in a complex formation between the pigment and the peptide which might be the reason for a more even hair coloration and longer lasting coloring results.

Further on, in another preferred modification of the invention the hair conditioning composition can be characterized in that the critical micelle concentration of the water soluble oligo-peptide is ≤5%. More preferably the critical micelle concentration of the water soluble oligo-peptide is ≤3% and most preferably the critical micelle concentration of the water soluble oligo-peptide is ≤2%. The critical micelle concentration (CMC) is defined as the concentration of molecules in an aqueous solution above which micelles are formed and almost all additional molecules added to the system go to the micelles. The CMC is an important characteristic of a surfactant or of surface active compounds. Without being bound by the theory it is assumed, that the interaction of the oligo-peptide and the dye in the hair color composition is positively influenced by oligo-peptides exhibiting a low critical micelle concentration.

In another aspect of the invention the proteinous raw-material source containing Sulfur may be selected from Garbanzo beans, kidney beans, lentils, lima beans, navy beans, soybeans, Barley, brown rice, buckwheat, millet, oatmeal, quinoa, rye, wheat germ, wheat, wild rice, wool, feathers, hair or horn. Especially preferred are keratinous raw-materials including, for example, animal hairs, human hair, feathers, hooves, claws, horns, scales and the like. Of these, wool, human hair and feathers are preferably used. These keratin materials may be subjected to the oxidation or reduction reaction as they are but if necessary, they may be cut or reduced into pieces having a suitable size or subjected to pretreatments such as washing and de-fatting.

In a further preferred embodiment of the invention the conditioning composition is characterized in a way, that the oligo-peptide is obtainable by an alkaline hydrolysis process comprising:
  a) suspending the proteinous material in water;
  b) adding a chelating agent to the aqueous protein suspension;
  c) adding an alkali to the aqueous protein suspension;
  d) heating the suspension to a temperature ≥60° C.;
  e) adjusting the pH of the mixture between ≥pH 2 and ≤pH 10 and
  f) filtration of the mixture.

Without being limited by theory it is assumed, that especially the structure and function of the oligo-peptide may be determined by the special hydrolysis process. Important structural features like the molecular weight distribution and structural features of the amino-acid side chains may be determined by this process. The alkali used for the hydrolysis can be any inorganic alkali such as sodium hydroxide, potassium hydroxide, lithium hydroxide, barium hydroxide, sodium carbonate, potassium carbonate, lithium carbonate, sodium silicate, borax and the like.

The acid used in e) may be of organic and/or inorganic origin or a mixture thereof. Some of them to mention are phosphoric acid, hydrochloric acid, sulfuric acid, nitric acid as the inorganic ones and to the organic acids the well known citric acid and lactic acid, glycolic acid, hydroxyacrylic acid, glyceric acid, malic acid and tartaric acid and of the dicarboxylic acids are malonic acid, succinic acid, glutaric acid, adipic acid, maleic acid, fumaric acid and phtalic acid.

In an especially preferred embodiment of the invention the hair conditioning composition is characterized in that the oligo-peptides are chemically modified by the use of phosphoric acid or phosphoric acid esters.

In another favored form of the hair conditioning composition the composition further comprises hair coloring agents and/or hair conditioning ingredients and/or cosmetic oils and/or surface active agents and/or buffers. Some examples for hair coloring agents which might be used with the hair conditioning composition of the present invention have been given above.

In addition the composition may include oil and fat, wax, hydrocarbon oil, higher fatty acid, higher alcohol, ester oil, silicone oil, anionic surfactant, cationic surfactant, ampholytic surfactant, nonionic surfactant, UV absorbers, polyhydric alcohol, metal ion sequestrant, sugar, amino acid, organic amine, polymer emulsion, pH controlling agent, skin nutrient, vitamin, antioxidant, antioxidation promoter, and fragrance. These ingredients may be optionally suitably incorporated, and the hair styling cosmetic composition of the invention can be produced according to the intended preparation form thereof in an ordinary manner.

In addition further natural or synthetic hydrocolloid-forming polymers may be incorporated, including water-soluble, natural or synthetic polymers which form gels or viscous solutions in aqueous systems. They are advantageously selected from further natural polysaccharides, synthetically modified derivatives thereof or synthetic polymers. Examples of further polysaccharides include homoglycans or heteroglycans, for example carragheen, pectins, tragacanth, guar gum, locust bean flour, agar-agar, gum arabic, xanthan gum, natural and modified starches, dextrans, dextrin, maltodextrins, glucans, such as beta-1,3-glucan, beta-1,4-glucan, such as cellulose, mucopolysaccharides, such as especially hyaluronic acid, etc. Examples of synthetic polymers include: cellulose ethers, polyvinyl alcohol, polyvinylpyrrolidone, synthetic cellulose derivatives, such as methylcellulose, carboxycellulose, carboxymethylcellulose, especially sodium carboxymethylcellulose, cellulose esters, cellulose ethers such as hydroxypropylcellulose, polyacrylic acid, polymethacrylic acid, poly(methyl methacrylate) (PMMA), polymethacrylate (PMA), polyethylene glycols, etc. It is also possible to use mixtures of these polymers.

It is further advantageous, that the hair care composition might contain solid plant extracts, micronized plant extracts, liquid plant extracts, hydrophilic plant extracts, lipophilic plant extracts, individual constituents of plants; and mixtures thereof. These extracts might contain flavonoids and their analogues; rutin, quercertin, diosmin, hyperoside, (neo) hesperidine, hesperitin, ginkgo biloba (e.g. ginkgoflavone glycosides), crataegus extract (e.g. oligomeric procyanidines), buckwheat (e.g. rutin), *Sophora japonica* (e.g. rutin), birch leaves (e.g. quercertin glycosides, hyperoside and rutin), elder blossom (e.g. rutin), linden blossom (e.g. essential oil with quercertin and farnesol), hypericon oil (e.g. olive oil extract), calendula, arnica (e.g. oily extracts of the blossom with essential oil, polar extracts with flavonoids), melissa (e.g. flavones, essential oil); immune stimulants: *Echinacea purpurea* (e.g. alcoholic extracts, fresh sap, pressed juice), *Eleutherokokkus senticosus*; alkaloids: rauwolfia (e.g. prajmaline), evergreen (e.g. vincamine); further phytopharmaceuticals: aloe, horse chestnut (e.g. aescin), garlic (e.g. garlic oil), pineapple (e.g. bromelains), ginseng (e.g. ginsenosides), milk thistle fruits (e.g. extract standardised to silymarin), butcher's broom root (e.g. ruscogenin), baldrian (e.g. valepotriate, Tct. valerianae), kava kava (e.g. kavalactones), hop blossom (e.g. hop bitters), extr. passiflorae, gentian (e.g. ethanol, extract), anthraquinone-containing drug extracts, e.g. aloin-containing aloe vera juice, pollen extract, algae extracts, liquorice root extracts, palm extract, galphimia (e.g. mother tincture), mistletoe (e.g. aqueous-ethanol. extract), phytosterols (e.g. beta-sitosterol), mullen flowers (e.g. aqueous-alcohol. extract), drosera (e.g. liqueur wine extract), sea buckthorn fruits (e.g. juice extracted therefrom or sea buckthorn oil), marshmallow root, primrose root extract, fresh plant extracts from mallow, comfrey, ivy, horsetail, yarrow, ribwort (e.g. pressed juice), stinging nettle, celandine, parsley; plant extracts from *Norolaena lobata, Tagetes lucida, Teeoma siems, Momordica charantia*, and aloe vera.

Further on auxiliary substances might be present in the hair conditioning composition Auxiliary substances include: pH-adjusting agents, buffering substances, preserving agents, softening agents, lubricants listed in the group of active agents, inorganic and organic acids or bases mineral waxes, such as microcristalline waxes, synthetic waxes, such as polyethylene waxes or silicone waxes, as well as oils that are suitable for cosmetic purposes (so-called cosmetic oils), such as, for example, those mentioned in the CTFA treatise entitled "Cosmetic Ingredient Handbook", 1st edition, 1988.

The hair conditioning composition of the present invention might be in any cosmetically or pharmaceutically acceptable form. It is preferred, that the cosmetic preparations may be in the form of a powder, lotion, hydrogel, oil, emulsion, micro-emulsion, nano-emulsion, triple-emulsion, paste, polish, dry powder, dry sheet, freeze dried composition or cream. It is especially preferred, that the hair care composition is in the form of a solution, emulsion, suspension or gel.

The hair conditioning composition can be favorably used in a hair-coloration treatment. The usage might be characterized in that the hair conditioning composition is added to the hair directly before the coloration process. For instance, the hair conditioning composition might be applied to the wet hair after a washing step before the color treatment is performed or the hair conditioning composition might also be used in the washing step. Here it might be favorable, that additional surface active agents might be present.

In another aspect of the invention the hair conditioning composition might be added to the hair coloration composition before the coloration process. Instead of pre-treating the hair with the hair conditioning composition, the beneficial effects can also be achieved by mixing the hair coloring composition with the hair conditioning composition for instance in a bowl and add the composition to the hair in a single step. This procedure might be performed either after a short equilibration time in the bowl or directly after thoroughly mixing of both compositions.

In order to ease the overall application and to provide a full solution to the end user it is advantageously to offer a kit of parts for hair care cosmetic use containing the hair conditioning composition and/or a hair shampoo and/or a hair coloring solution and/or a hair rinse solution and/or a hair straightening composition and/or a hair curing composition and/or a hair repair composition. The kit can be designed to be sold directly to end-consumers in an over the counter way (OTC-kit) or it can be intended to provide special solution to hair care professionals. It can be desirable that the hair conditioning composition might be separately packed within the kit-of-parts or might be blended in one container with one of the above mentioned compositions.

DETAILED DESCRIPTION OF THE PREFERRED EMBODIMENTS

The invention is described further by the following embodiments, figures and the corresponding explanations.

In a comparative test hair test samples were treated with conventional coloring compositions (Wella hair colors) and with a combination of the conventional hair coloring compositions and the inventive hair conditioning composition for permanent and semi-permanent hair color application ("CC"). The improvement of color intensity has been determined by L*a*b color measurement analysis, wherein $\Delta E_{p,v} = \sqrt{(L_p^* - L_v^*)^2 + (a_p^* - a_v^*)^2 + (b_p^* - b_v^*)^2}$. The results are shown Tab. 1.

TABLE 1

| Hair Dye number | L* | a* | b* | ΔE |
|---|---|---|---|---|
| 55/46 | 41.7 | 28.8 | 17.7 | 18.4 |
| 55/46 + CC | 29.6 | 30.6 | 31.4 | |
| 6/11 | 38.6 | −1.0 | 4.6 | 6.9 |
| 6/11 + CC | 31.9 | 0.0 | 6.4 | |
| 8/73 | 55.6 | 4.6 | 20.7 | 16.9 |
| 8/73 + CC | 39.0 | 6.6 | 19.1 | |
| 5/75 | 37.6 | 7.0 | 5.1 | 7.5 |
| 5/75 + CC | 30.8 | 4.4 | 3.9 | |
| 55/44 | 46.1 | 18.9 | 8.0 | 2.1 |
| 55/44 + CC | 45.2 | 18.1 | 6.3 | |
| 8/45 | 67.3 | 19.9 | 14.0 | 3.6 |
| 8/45 + CC | 66.7 | 17.3 | 11.5 | |
| 6/6 | 60.4 | 12.4 | 4.1 | 1.7 |
| 6/6 + CC | 61.0 | 19.9 | 4.5 | |
| 8/7 | 70.2 | 4.5 | 13.0 | 10.4 |
| 8/7 + CC | 60.1 | 6.1 | 14.3 | |
| 5/4 | 60.9 | 6.1 | 10.7 | 8.6 |
| 5/4 + CC | 52.4 | 6.4 | 9.2 | |

Assessment: ΔE: 0.0-0.5 nearly no difference; 0.5-1.0 difference can be realized by practiced eye; 1.0-2.0 appreciable color difference; 2.0-4.0 perceived color difference; ≥4.0 substantial color difference.

Figure 1:
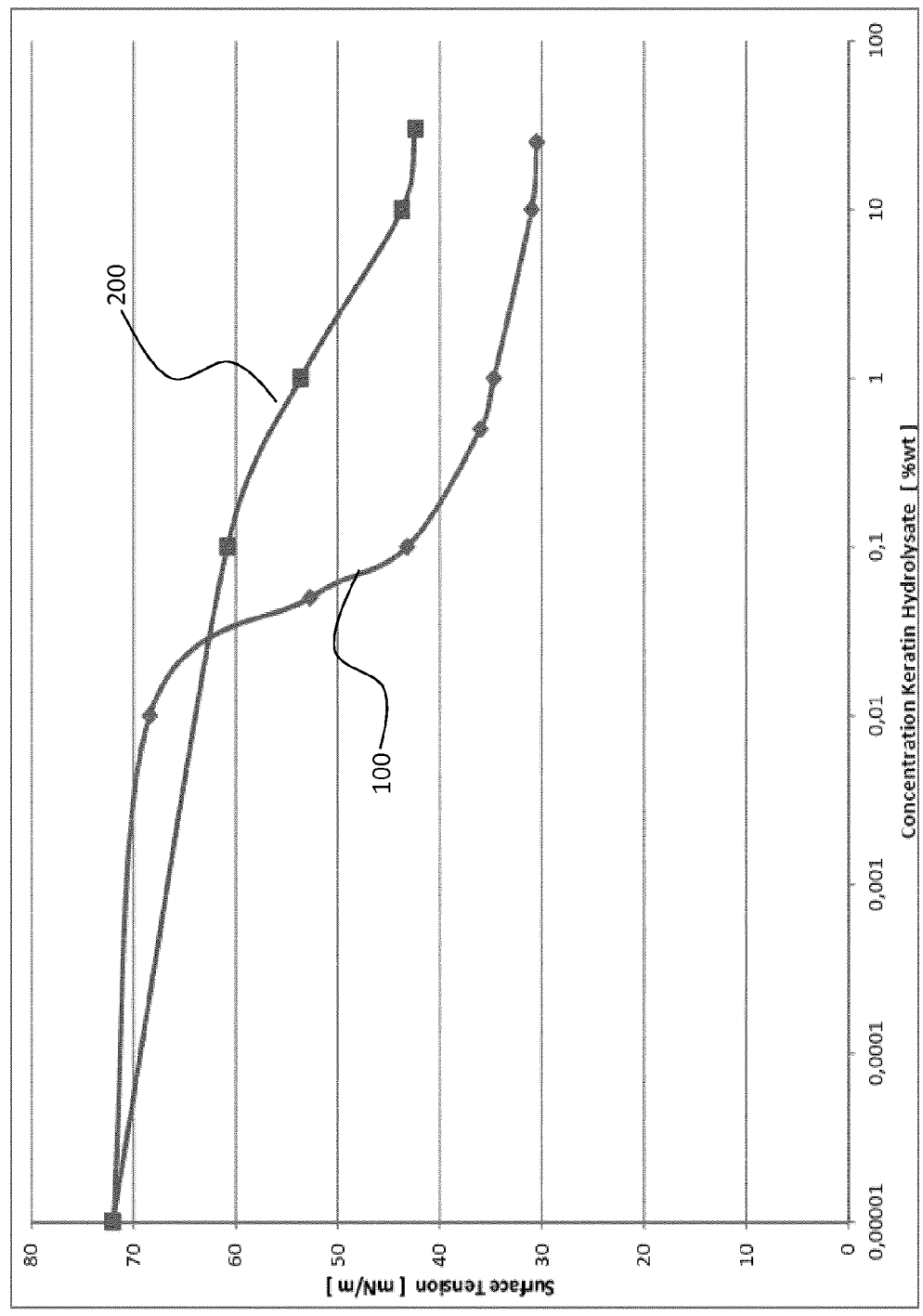
FIG. 1 shows the surface tension as a function of the concentration of an aqueous solution of an oligo-peptide as used in the inventive hair conditioning composition.

According to an preferred embodiment of the invention, the oligo-peptides preferably used in the inventive hair conditioning composition for permanent and semi-permanent hair color application, like, e.g. keratin hydrolysates, have a critical micelle concentration (CMC) in a range of ≤2%. Thus the CMC of the oligo-peptides used in the inventive composition is substantially lower than the CMC of oligo-peptides known from the prior art. Such a low CMC contributes to improved efficiency of the inventive composition in washing processes. FIG. 1 shows the surface tension of an aqueous solution as a function of concentration of an inventively used oligo-peptide, i.e. a keratin hydrolysate, 100 and a comparative keratin hydrolysate 200 (Kera Tein, Tri-K Industr.) at a temperature of 25° C. The critical micelle concentration is obtained from the ordinate value of the inflection point of the respective concentration gradient. As can be seen, the inventively used oligo-peptide shows a CMC value which is about two orders of magnitude lower in comparison to the reference product. Considering an average molecular weight in the range of 3000 Da to 7000 Da results in a CMC in the range of from about ≥0.05 mM to 0.5 mM.

Figure 2A:
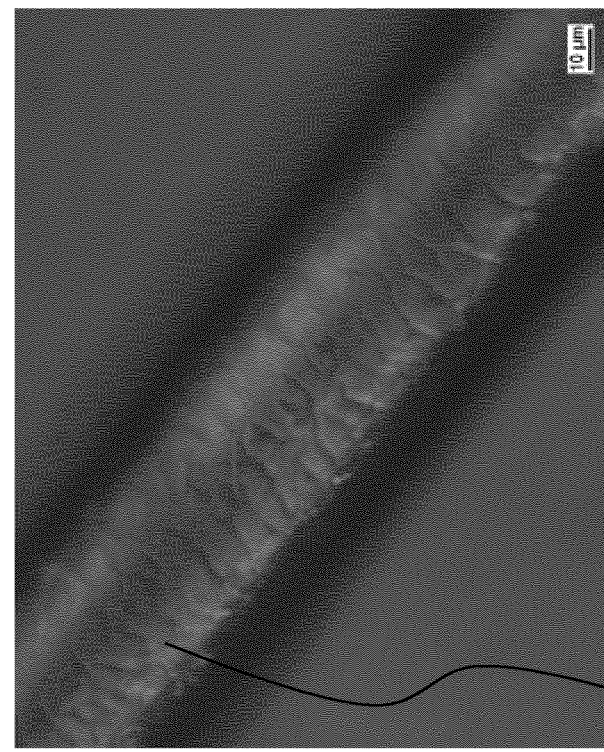
FIG. 2A shows a magnified image of hair treated with a conventional coloring composition and FIG. 2B shows hair after treatment with a coloring composition in combination with an inventive hair conditioning composition.
Figure 2B:
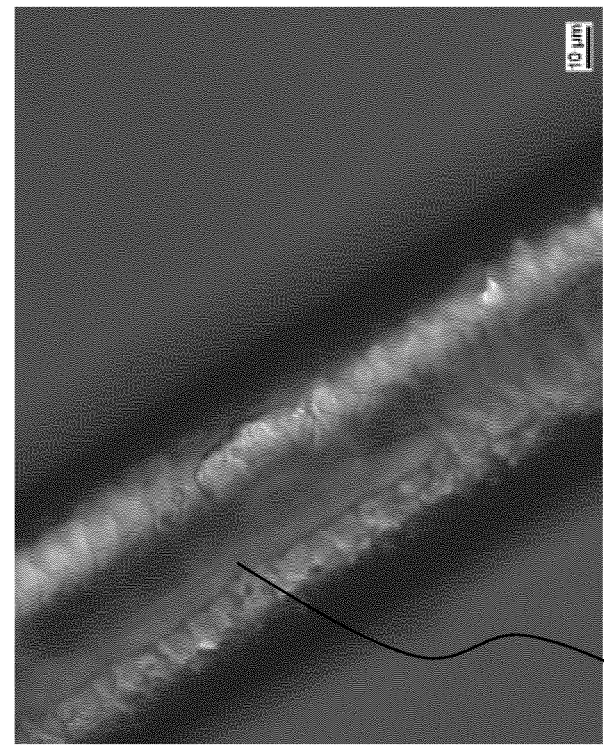

FIG. 2A shows a magnified image of hair treated with a conventional coloring composition and FIG. 2B shows hair after treatment with a coloring composition in combination with an inventive hair conditioning composition. FIG. 2A and FIG. 2B are magnified images (400× magnification) of one and the same persons hair. For the analysis the hair has been treated in a half side test by a conventional coloring product (FIG. 2A) and a coloring composition in combination with an inventive hair conditioning composition. The test was performed with 40 test persons. After three time shampooing 20 single hairs have been taken from the test persons head and been analyzed. FIG. 2A and FIG. 2B are representative images of the results. While the hair treated with conventional coloring compositions in FIG. 2A shows damaged areas 300, in FIG. 2B the surface of the hair treated with the inventive composition is even and free of visible damages.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The invention claimed is:

1. A hair conditioning composition for permanent and semi-permanent hair color applications, the hair conditioning composition comprising:
    a solvent,
    a water-soluble, oligo-peptide from a natural proteinaceous raw-material source containing sulfur which is selected from the group consisting of keratin hydrolysates,
    alkaline or alkaline earth metal ions,
    a multidentate ligand or chelating agent, and optionally
    a redox-active inorganic or redox-active organic component,
wherein an aqueous solution of the keratin hydrolysate has a critical micelle concentration at 25° C. in the range of from ≥0.05 mM to 0.5 mM, and
wherein the average molecular weight of the keratin hydrolysate is in the range of 3000 Da to 7000 Da.

2. The hair conditioning composition according to claim 1, wherein the hair conditioning composition exhibits a negative redox-potential in the range between −1000 mV and −10 mV.

3. The hair conditioning composition according to claim 1, wherein the hair conditioning composition further comprises a quaternary cationic surface active agent.

4. The hair conditioning composition according to claim 1, wherein the solvent is selected from the group consisting of water, alcohols having 1-5 carbon atoms, and any mixture thereof.

5. The hair conditioning composition according to claim 1, wherein the hair conditioning composition contains from 1% (w/w) to 10% (w/w) of the water-soluble oligo-peptide.

6. The hair conditioning composition according to claim 1, wherein the natural, proteinaceous raw-material source containing sulfur is selected from the group consisting of garbanzo beans, kidney beans, lentils, lima beans, navy beans, soybeans, barley, brown rice, buckwheat, millet, oatmeal, quinoa, rye, wheat germ, wheat, wild rice, wool, feathers, hair and horn.

7. The hair conditioning composition according to claim 1, wherein the oligo-peptide is obtained by an alkaline hydrolysis process comprising:
    suspending the proteinaceous material in water;
    adding a chelating agent to the aqueous protein suspension;
    adding an alkali to the aqueous protein suspension;
    heating the suspension to a temperature ≥60° C.;
    adjusting the pH of the mixture between pH 2 and pH 10; and
    filtering the mixture.

8. The hair conditioning composition according to claim 1, wherein the oligo-peptide is chemically modified by the use of phosphoric acid or phosphoric acid esters.

9. The hair conditioning composition according to claim 1, wherein the hair conditioning composition further comprises a hair coloring agent, a hair conditioning ingredient, an oil, a surface active agent, or a buffer.

10. The hair conditioning composition according to claim 1, wherein the hair care composition is in the form of a solution.

11. The hair conditioning composition according to claim 1, wherein the hair care composition is in the form of an emulsion, suspension or gel.

12. The hair conditioning composition according to claim 1, wherein the solvent is propylene glycol.

13. The hair conditioning composition according to claim 1, wherein the solvent is glycerine.

14. A method of conditioning hair comprising applying the hair conditioning composition according to claim 1 onto the hair.

15. The method according to claim 14, wherein the hair conditioning composition is applied to the hair before a coloration process.

16. The method according to claim 14, wherein the composition is applied to the hair in a hair coloration treatment.

17. A kit of parts for hair care containing
    A) a hair conditioning composition comprising:
        a solvent,
        a water-soluble, oligo-peptide from a natural proteinaceous raw-material source containing sulfur which is selected from the group consisting of keratin hydrolysates,
        alkaline metal ions or alkaline earth metal ions,
        a multidentate ligand or chelating agent, and optionally
        a redox-active inorganic component or a redox-active organic component, wherein
        an aqueous solution the keratin hydrolysate has a critical micelle concentration at 25° C. in the range of from ≥0.05 mM to 0.5 mM, and wherein the average molecular weight of the keratin hydrolysate is in the range of 3,000 Da to 7,000 Da, and
    B) a hair treatment composition selected from the group consisting of a hair shampoo, a hair coloring solution, a hair rinse solution, a hair straightening composition, a hair curing composition, a heat repair composition and any combination thereof.

18. The kit of parts for hair care according to claim 17, wherein component B is a hair coloring solution for permanent and semi-permanent hair color applications.

* * * * *